(12) United States Patent
Lorenz (10) Patent No.: US 7,893,251 B2
(45) Date of Patent: Feb. 22, 2011

(54) METHODS FOR SELECTIVE ISOLATION OF NUCLEIC ACIDS FROM MICROBIAL CELLS PRESENT IN SAMPLES CONTAINING HIGHER EUKARYOTIC CELLS AND/OR TISSUES

(75) Inventor: Michael G. Lorenz, Bad Zwischenahn (DE)

(73) Assignee: Molzym GmbH & Co. KG, Bremen (DE)

( * ) Notice: Subject to any disclaimer, the term of this patent is extended or adjusted under 35 U.S.C. 154(b) by 16 days.

(21) Appl. No.: 11/885,256

(22) PCT Filed: Feb. 28, 2006

(86) PCT No.: PCT/EP2006/001845

§ 371 (c)(1),
(2), (4) Date: Aug. 29, 2007

(87) PCT Pub. No.: WO2006/092278

PCT Pub. Date: Sep. 8, 2006

(65) Prior Publication Data

US 2008/0160528 A1 Jul. 3, 2008

(30) Foreign Application Priority Data

Mar. 2, 2005 (DE) ................... 10 2005 009 479

(51) Int. Cl.
*C12N 9/16* (2006.01)
(52) U.S. Cl. .................................... 536/25.4
(58) Field of Classification Search .............. 536/25.4
See application file for complete search history.

(56) References Cited

U.S. PATENT DOCUMENTS

| 5,364,763 A | * | 11/1994 | Kacian | ....................... 435/7.32 |
| 6,291,248 B1 | | 9/2001 | Haj-Ahmad | |
| 2003/0118989 A1 | * | 6/2003 | Rosenow et al. | ................ 435/6 |
| 2003/0215845 A1 | * | 11/2003 | Bille | ............................. 435/6 |
| 2005/0009913 A1 | * | 1/2005 | Mohr | ......................... 514/561 |

OTHER PUBLICATIONS

International Search Report for PCT/E2006/001845 mailed Jul. 6, 2006.
Disqué et al., "Automatisierte Probenvorbereitung für die PCRDiagnostik von Sepsis," Biospektrum, [Online] No. 1, 2006, pp. 1-2, XP002384695, retrieved from the Internet: URL:http://www.molzym.com/pdf/IA_Fuji.pdf, [retrieved on Jun. 8, 2006].
Blood DNA removal and bacterial isolation kit MolYsis Plus5—5 ml blood protocol, retrieved Sep. 6, 2006 from http://www.molzym.de/pdf/MolYsis_Plus5_0106_Print.pdf, Jan. 2006, XP002384962.
"OmniCleave? Endonuclease, Cat. Nos. OC7810K and OC7850K," [Online] Jan. 2004, XP002384696, retrieved from the Internet: URL:http://www.epibio.com/pdftechlit/100p1014.pdf [retrieved on Jun. 8, 2006].
Shortle, "Guanidine Hydrochloride Denaturation Studies of Mutant Forms of Staphylococcal Nuclease," Journal of Cellular Biochemistry, vol. 30, No. 4, 1986, pp. 281-290, XP002384697.
Sambrook et al., "Molecular Cloning—A laboratory manual third Edition," 2001, Cold Spring Habour Laboratory Press, New York, pp. 7.4-7.8, 7.85, XP002384968.
Boom et al., "Rapid and Simple Method for Purification of Nucleic Acids," Journal of Clinical Microbiology, vol. 28, No. 3, Mar. 1, 1990, pp. 495-503, XP000607196.
Burke et al., "Isolation Characterization and Activation of the Magnesium Dependent Endo DNase from Bacillus-Subtilis," Biochemistry, vol. 16, No. 3, 1977, pp. 403-410, XP002384698.
"ReadyPreps? Protein Preparation Kit Product Information Catalog No. RP78100," [Online], Jan. 2006, XP002384967, retrieved from the Internet: URL:http://www.ebiotrade.com/buyf/productsf/epicentre/relation/readypreps.pdf, [retrieved on Jun. 9, 2006].
Jekel et al., "The periplasmic endonuclease I of *Escherichia coli* has amino-acid sequence homology to the extracellular DNases of *Vibrio cholerae* and *Aeromonas hydrophila*," Gene, vol. 154, No. 1, Feb. 27, 1995, pp. 55-59, XP004042502.
Smith et al., "Comparison of commercial DNA extraction kits for extraction of bacterial genomic DNA from whole-blood samples," Journal of Clinical Microbiology, Jun. 2003, vol. 41, No. 6, Jun. 2003, pp. 2440-2443, XP002384961.
PCR-Diagnosis of Blood Pathogens: Size Matters, retrieved from http://www.chemie.de/products/e/54806, found on Aug. 6, 2006, Chemie.DE Information Service GmbH, XP002384699.
Directed isolation of bacterial DNA from whole blood Pre-analytic tool for the reliable diagnosis of sepsis by broad-range and multiplex PCR, retrieve from http://www.molzym.com/home_e.htm, found on Aug. 6, 2006, XP002384700.
Conlan et al, "Modulating restriction endonuclease activities and specificities using neutral detergents", BioTechniques (1999), 27(5), 955-958, 960.
Kim, "Purification and Characterization of DNA Repair Endonucleases from Mammalian Cells", (1991), 51(9) 4192.
RNA Extraction Protocol for Basal Angiosperms, Rev. Aug. 25, 2003.

* cited by examiner

*Primary Examiner*—Kenneth R. Horlick
(74) *Attorney, Agent, or Firm*—Nixon & Vanderhye P.C.

(57) ABSTRACT

The invention relates to the use of nucleases, especially DNA-degrading nucleases, for degrading nucleic acids in the presence of one or several chaotropic agents and/or one or several surfactants. The invention further relates to a method for purifying RNA from mixtures of DNA and RNA as well as kits for carrying out such a method. Also disclosed is a method for specifically isolating nucleic acids from microbial cells provided in a mixed sample which additionally comprises higher eukaryotic cells as well as kits for carrying out such a method.

21 Claims, 5 Drawing Sheets

METHODS FOR SELECTIVE ISOLATION OF NUCLEIC ACIDS FROM MICROBIAL CELLS PRESENT IN SAMPLES CONTAINING HIGHER EUKARYOTIC CELLS AND/OR TISSUES

This application is the US national phase of international application PCT/EP2006/001845 filed 28 Feb. 2006, which designated the U.S. and claims benefit of DE 10 2005 009 479.1, filed 2 Mar. 2005, the entire contents of each of which are hereby incorporated by reference.

The invention relates to the use of nucleases, in particular of DNA-degrading nucleases, for degrading nucleic acid in the presence of one or more chaotropic agents and/or one or more surfactants. The present invention further relates to a method of purification of RNA from mixtures of DNA and RNA and kits for carrying out said method. The invention further relates to a method for the selective isolation of nucleic acids from microbial cells that are present in a composite sample that additionally comprises higher eukaryotic cells, and kits for carrying out said method.

The isolation and purification of nucleic acids from biological materials represent a fundamental technique in the area of sample preparation for molecular-biological analysis and diagnosis in human or veterinary medicine. For example, it is desirable for infections or predisposition to diseases to be detected quickly and reliably, so as to be able to initiate appropriate therapy. However, techniques of molecular-biological analysis and diagnosis also play an important role in other fields, for instance in animal and plant breeding, plant protection, forensics, biotechnology and molecular-biological research.

In the state of the art, nucleic acids are usually separated from cells and tissues with the aid of strongly denaturing and reducing agents. Chaotropic agents, for example guanidine salts, regularly find application. These salts, which have a strong denaturing action, lead on the one hand to cell disruption and, on the other hand, ensure that enzymes that would lead to degradation of the nucleic acids released from the cells are inactivated.

A disadvantage of using chaotropic agents for cell disruption is the fact that subsequent enzymatic process steps can only take place after removing these agents from the preparation. For example, in RNA purification that is carried out using chaotropic salts for cell disruption, these chaotropic salts must be removed first, before contaminating DNA can be degraded enzymatically by the action of pancreatic DNase I. However, this procedure involves increased expenditure of time and materials, as at least one additional process step (e.g. filtration) must be carried out.

Subsequently, appropriate methods can be used for removing other cellular constituents from the nucleic acids released, and purifying the latter. The nucleic acids, once released, can be purified for example by phenol-chloroform extraction (Sambrook, J., Russell, D. W. (2001): Molecular cloning—a laboratory manual. Cold Spring Harbor Laboratory Press, Cold Spring Harbor, N.Y.) or by selective binding to a suitable support material. Mineral support materials in particular, for example ground glass powder, diatomaceous earth or silica materials, have proved suitable as support materials in the past, and chemically modified materials such as silica carbide (U.S. Pat. No. 6,291,248) can also be used. Kits for the purification of nucleic acids are currently available from various companies, e.g. Molzym GmbH & Co KG (Bremen, DE), Qiagen (Hilden, DE), Macherey-Nagel (Düren, DE) or Sigma (Deisenhofen, DE). As a rule all these methods ensure a degree of purity of the nucleic acids that is found to be adequate for subsequent analytical and diagnostic techniques.

A substantial part of molecular-biological diagnosis of various pathogens (for example the detection of pathogenic bacteria, yeasts, fungi, protozoa or viruses) is now achieved in clinical practice using methods that are based on the amplification of nucleic acids (DNA or RNA) of the respective pathogen.

For this purpose, PCR primers are used for detecting species-specific and strain-specific nucleotide sequences of the pathogen. In bacteria, for example, these specific nucleotide sequences can comprise IS-elements, pathogenicity factors, species-specific genomic sequences or also certain, less conserved (genus-specific or species-specific) regions on the bacterial 16S or 23S rRNA gene. At present, numerous bacterial pathogens, especially pathogens that can only be cultivated inadequately or extremely expensively using existing cultivation techniques, are identified in clinical practice by amplification techniques by means of strongly conserved regions in the gene of the 16S-rRNA. These pathogens include, among others, various species of the genera *Mycobacterium, Enterococcus, Streptococcus, Staphylococcus, Salmonella, Legionella, Chlamydia* and *Shigella*.

However, the nucleic acid amplification techniques used for detection are often extremely susceptible to failure, as the pathogens that are to be detected are, as a rule, mixed with various other types of cells (for example the patient's blood or tissue cells) in sample material being investigated. Nucleic acid preparations obtained from these composite samples normally contain a mixture of nucleic acids from all cell types that were present in the composite sample. This can have the effect that when such nucleic acid preparations are used in the amplification techniques carried out for the purpose of pathogen diagnosis, nonspecific amplification products are formed that make molecular diagnosis more difficult or even impossible. For example, in nucleic acid preparations from composite samples that also contained human tissue cells along with bacterial cells, owing to the common evolutionary history of eukaryotic cellular organelles and the bacterial genome, nonspecific PCR products can be observed if specific primers for the gene of 16S-rRNA are used.

Problems of this kind also occur in detection techniques with nucleic acids from other composite samples with various types of cells, e.g. in the case of nucleic acid preparations from samples that were obtained from plant organisms and as a rule also contain plant cells and tissues in addition to a phytopathogenic bacterium that is to be detected.

The detection of pathogens by amplification of specific nucleic acids is, however, of considerable advantage for clinical diagnosis, because even pathogens that cannot be identified by the usual cultivation techniques can be determined by sequencing and comparing the results with gene bank entries. This is important in particular in the diagnosis of sepsis, because numerous blood colonizers that can cause this pathological condition cannot be detected by means of blood cultures.

The problem underlying the present invention is therefore to provide methods by use of which nucleic acid can be isolated selectively from microbial cells that are contained in composite samples with higher eukaryotic cells or tissues. A further problem underlying the present invention is to provide methods by use of which nucleic acid can be isolated selectively from blood products, in particular thrombocyte concentrates and erythrocyte concentrates, or from other body fluids, in particular aspirates (e.g. joint, eye), liquor and bronchial-alveolar lavage. A further problem underlying the present invention is to provide means by which nucleic acids can be degraded in a chaotropic environment. The above problems are solved according to the invention by the subject-matter of the present claims.

It was now found surprisingly found, that endonuclease I from *Escherichia coli* (SEQ ID NO:1), *Vibrio cholerae* (SEQ ID NO:2), *Erwinia chrysanthemi* (SEQ ID NO:3) and *Aeromonas hydrophila* (SEQ ID NO:4) are not denatured under chaotropic environmental conditions that lead to cell lysis, and thus retain their enzymatic activity. Accordingly, these nucleases are particularly suitable for the degradation of DNA in the presence of chaotropic agents and/or surfactants. The invention thus relates, according to a first aspect, to the use of a nuclease for degrading nucleic acid in the presence of one or more chaotropic agents and/or one or more surfactants. According to a particularly preferred embodiment, the invention relates to the use of a DNA-degrading nuclease for degrading DNA in the presence of one or more chaotropic agents and/or one or more surfactants.

According to another preferred embodiment, the nuclease is one of the aforementioned enzymes, wherein the use of endonuclease I from *Escherichia coli* (SEQ ID NO:1) is particularly preferred.

In connection with the present invention, the term "nucleic acid" denotes single-stranded, double-stranded and partially double-stranded ribonucleic acids (RNA) and deoxyribonucleic acids (DNA). Moreover, the term comprises duplex and triplex structures that can be formed from DNA and/or RNA.

The term "nuclease" denotes, within the scope of the present invention, an enzyme that effects hydrolytic cleavage of the ester bond between the 5'-phosphate group of a nucleotide and the 3'-hydroxyl group of the adjacent nucleotide in a nucleic acid and therefore accomplishes the degradation of a DNA or RNA molecule. Nucleases are known from numerous organisms. Nucleases cleave either RNA or DNA molecules to smaller units or even to their monomers.

Furthermore, enzymes are also known that display both activities. "DNA-degrading nuclease" is accordingly to be understood to mean a nuclease that is able to cleave single-stranded, double-stranded and partially double-stranded DNA molecules into smaller units or monomers. Such enzymes are also termed "DNases" in the state of the art.

The nuclease or DNA-degrading nuclease can be, according to the invention, an endonuclease or an exonuclease. Here, exonuclease means an enzyme that degrades a nucleic acid chain starting from one or from both ends of the chain. Conversely, the degradation of a nucleic acid chain mediated by endonucleases takes place starting from a position within the chain. It is preferred for the nuclease to be an endonuclease.

The endonuclease that is used according to the invention under chaotropic conditions can be, for example, endonuclease I (EndA) from *Escherichia coli* (Jekel, M., Wackernagel, W., J. Bacteriol. 176:1550, 1994). This enzyme is available from various suppliers, e.g. from Molzym GmbH & Co KG (Bremen, Germany). It can also be the nuclease from *Vibrio cholerae* shown in SEQ ID NO:2 (Focareta T., Manning P. A.; Gene 53 (1):31-40 (1987)). The nuclease from *Erwinia chrysanthemi* shown in SEQ ID NO:3 (Moulard M., Condemine G., Robert-Baudouy J.; Mol. Microbiol. 8(4): 685-695 (1993)) or the nuclease from *Aeromonas hydrophila* shown in SEQ ID NO:4 (Focareta T., Manning P. A.; Gene 53(1):31-40 (1987); Chang M.-C., Chang S.-Y., Chen S.-L., Chuang S.-M.; Gene 122 (1):175-180 (1992)) can also be used within the scope of the invention. According to a particularly preferred embodiment, the endonuclease is the polypeptide from *Escherichia coli* shown in SEQ ID NO:1. It was surprisingly found within the course of the present invention, that the above enzymes are capable of degrading DNA effectively under chaotropic conditions, i.e. in the presence of chaotropic agents and/or surfactants.

Existing enzymes known in the state of the art, such as pancreatic DNase I or nuclease from the bacterial genus *Serratia* (e.g. Benzonase, Merck), are inactivated under these conditions.

According to the invention, variants and derivatives of the polypeptides shown in SEQ ID NO:1, SEQ ID NO:2, SEQ ID NO:3 and SEQ ID NO:4 and enzymatically active fragments of the polypeptides and their variants are also included.

Variants of a polypeptide are to be understood as peptides or polypeptides that differ by one or more exchanges of amino acids from the amino acid sequence of the polypeptide shown in SEQ ID NO:1, SEQ ID NO:2, SEQ ID NO:3 or SEQ ID NO:4.

Basically, any amino acid residue of the amino acid sequences shown in SEQ ID NO:1 to SEQ ID NO:4 can be exchanged for a different amino acid, provided the resultant sequence of the variant is still an enzymatically active polypeptide with nuclease function. In particular, variants for which a total of up to 5%, 10%, 15%, 20%, 30%, or 40% of the amino acids differs from the amino acid sequence shown in SEQ ID NO:1 are included. Polypeptides in which one or more amino acids were inserted in the amino acid sequence of the polypeptide shown in SEQ ID NO:1, SEQ ID NO:2, SEQ ID NO:3 or SEQ ID NO:4, are also included as variants. Such insertions can be made at any position of the polypeptide shown in SEQ ID NO:1, SEQ ID NO:2, SEQ ID NO:3 or SEQ ID NO:4. Moreover, polypeptides in which one or more amino acids are missing, in comparison with the polypeptide shown in SEQ ID NO:1, SEQ ID NO:2, SEQ ID NO:3 or SEQ ID NO:4, are also considered to be variants of the polypeptides shown in SEQ ID NO:1, SEQ ID NO:2, SEQ ID NO:3 or SEQ ID NO:4. Such deletions can apply to any amino acid position of the sequence of SEQ ID NO:1, SEQ ID NO:2, SEQ ID NO:3 or SEQ ID NO:4.

Enzymatically active fragments of the sequence shown in SEQ ID NO:1, SEQ ID NO:2, SEQ ID NO:3 or SEQ ID NO:4 or variants thereof are to be understood to mean peptides or polypeptides that differ from the amino acid sequence shown in SEQ ID NO:1, SEQ ID NO:2, SEQ ID NO:3 or SEQ ID NO:4 or from the above-defined variants thereof, by the absence of one or more amino acids at the N-terminus and/or at the C-terminus of the peptide or polypeptide. Derivatives of the polypeptides shown in SEQ ID NO:1, SEQ ID NO:2, SEQ ID NO:3 and SEQ ID NO:4 or of the variants thereof denote in the present text, polypeptides that have structural modifications, for example modified amino acids, relative to a polypeptide shown in SEQ ID NO:1, SEQ ID NO:2, SEQ ID NO:3 or SEQ ID NO:4 or variants thereof.

These modified amino acids can be, according to the invention, amino acids that have been altered by phosphorylation, glycosylation, acetylation, thiolation, branching and/or cyclization. It is preferred that the variants or derivatives of the polypeptide shown in SEQ ID NO:1, SEQ ID NO: 2, SEQ ID NO:3 and SEQ ID NO:4 or the active fragments of this polypeptide or its variants have 75%, preferably up to 80%, 85%, 90% or even up to 99% of the activity of the polypeptide shown in SEQ ID NO:1, SEQ ID NO:2, SEQ ID NO:3 or SEQ ID NO:4.

Chaotropic agents are to be understood, within the scope of the present invention, as substances that disrupt regular molecular structures that are based on the formation of hydrogen bonds. Chaotropic substances destabilize the conformation of macromolecules by preventing formation of the $H_2O$ cage structures that are necessary for solvation. Chaotropic salts display high affinity for water and therefore form a large hydration shell. Chaotropic agents (such as chaotropic salts) are well known to a person skilled in the art (cf. guanidine hydrochloride, guanidine isothiocyanate, sodium perchlorate, sodium iodide, trichloroacetate, urea, rhodanite salt.

The chaotropic agents in whose presence the nuclease according to the invention can be used comprise in particular chaotropic salts, for example guanidine hydrochloride, sodium iodide, guanidine isothiocyanate or mixtures thereof.

Moreover, the nuclease according to the invention can also be used in the presence of one or more surfactants for degrading nucleic acids. "Surfactants" mean, in the present text, surface-active substances which concentrate preferentially at the interface of two media, e.g. at the water/air boundary. Anionic, cationic, amphoteric or nonionic surfactants can be used according to the invention.

Anionic surfactants have a negative charge of the molecule and comprise e.g. alkylbenzene sulfonates and alkane sulfonates. Cationic surfactants bear a positive charge and comprise e.g. distearyl dimethylammonium chloride. Nonionic surfactants have no charge and comprise fatty alcohol ethoxylates and alkyl polyglucosides. Amphoteric surfactants carry both a positive and a negative charge and comprise for example betaines. Surfactants in whose presence the nuclease can be used within the scope of the present invention comprise for example sodium dodecyl sulfate (SDS), BRIJ 40, Tween-20, deoxycholate, Triton X-100 or mixtures of said surfactants in various proportions.

Within the scope of the present invention it is preferred that the total concentration of the chaotropic agents in the reaction batch is from 0.1 mol/l to 2.5 mol/l, with a range of 0.5 mol/l-2 mol/l and a range of 1 mol/l-1.5 mol/l being particularly preferred. This means that the concentration of a chaotropic salt such as guanidine hydrochloride or guanidine isothiocyanate can be up to 0.1 mol/l, 0.5 mol/l, 1 mol/l, 1.5 mol/l, 2 mol/l or 2.5 mol/l, provided this salt is used as the only chaotropic substance in the reaction batch.

If mixtures of several chaotropic agents are used, for example mixtures of guanidine hydrochloride or guanidine isothiocyanate, then the total concentration of chaotropic agents should according to the invention be in the stated ranges.

The total amount of surfactant that can be used without causing inactivation of the nuclease can be, according to the invention, up to 2 wt. % of the total mixture. According to a preferred embodiment the total amount of surfactant in the reaction batch is 0.1-2 wt. %, and amounts of 0.5-1.5 wt. % and 1.2-1.4 wt. % are particularly preferred.

It is of course also possible to use mixtures of chaotropic agents (such as chaotropic salts) and surfactants. In these cases the amount of surfactant and the concentration of the chaotropic substance must be suitably adjusted to one another to ensure that the nuclease remains functional. A person skilled in the art can find out, using simple tests, which chaotropic substance(s) can be used at what concentration together with which surfactant(s).

Owing to the unexpected property of displaying activity even in the presence of chaotropic agents, the nucleases according to the invention can be used advantageously in numerous technical fields. For example, DNA-degrading nucleases can be used for the selective isolation—described below—of nucleic acid from composite samples comprising microbial cells and higher eukaryotic cells and/or tissues. Furthermore, DNA-degrading nucleases can be used selectively for the degradation of contaminating DNA in the course of RNA isolation. The isolation of RNA is carried out regularly under chaotropic conditions, with expensive buffering for removing DNA. This buffering becomes unnecessary when using a DNA-degrading nuclease that is stable under chaotropic conditions. Expenditure of time and materials can thus be reduced considerably.

Thus, according to a further aspect, the present invention relates to a method for the isolation and/or purification of RNA from mixtures comprising RNA and DNA, comprising
a) degrading the DNA using a DNA-degrading nuclease in the presence of one or more chaotropic agents and/or one or more surfactants; and
b) isolating and/or purifying the RNA by suitable methods.

According to a preferred embodiment of the invention, the DNA-degrading nuclease is an endonuclease. According to a particularly preferred embodiment the endonuclease has the amino acid sequence shown in SEQ ID NO:1, SEQ ID NO:2, SEQ ID NO:3 or SEQ ID NO:4, wherein the variants and derivatives, as defined above, of the polypeptide shown in SEQ ID NO:1, SEQ ID NO:2, SEQ ID NO:3 or SEQ ID NO:4 and enzymatically active fragments of the polypeptide and variants thereof also being included. According to a particularly preferred embodiment the endonuclease is the endonuclease from *Escherichia coli* shown in SEQ ID NO:1.

According to a preferred embodiment of the invention, the chaotropic agents are chaotropic salts. Preferably the chaotropic salts are guanidine hydrochloride, guanidine isothiocyanate and/or sodium iodide. According to a further embodiment the surfactants are sodium dodecyl sulfate, Brji40, Triton X-100 and/or Tween-20.

The total concentration of the chaotropic agents and the total amount of surfactants correspond to the concentrations and amounts stated above.

The DNA-degrading nuclease can be part of a buffer that comprises the appropriate chaotropic agents and/or surfactants, or can be added to such a buffer in the course of the reaction, for example after cell disruption.

The RNA that remains in the reaction batch after incubation with the DNA-degrading nuclease can be purified according to existing methods, for example using spin columns, such as are available from, among others, the company Molzym (Bremen, DE) as PrestoSpin R.

Accordingly, the present invention further relates to a method for the selective isolation of nucleic acids from microbial cells that are present in a composite sample that also comprises cells and/or tissues of higher eukaryotes, comprising
a) carrying out lysis of the higher eukaryotic cells and/or tissues, wherein the microbial cells substantially remain intact;
b) separating the microbial cells from the lysed eukaryotic cells and/or tissues;
c) carrying out lysis of the microbial cells, so that the nucleic acids are released from these cells;
d) isolating the nucleic acids released in step c).

The present invention provides a method for the selective isolation of nucleic acid from microorganisms. The microbial cells can be in a mixture (e.g. a fluid sample), which additionally contains cells and/or tissues of eukaryotic origin.

Moreover, the method according to the invention is suitable for isolating nucleic acid from blood products, in particular thrombocyte concentrates and erythrocyte concentrates, or from other body fluids, in particular aspirates (e.g. joints, eyes), liquor and bronchial-alveolar lavage. Within the scope of the present invention the term "method for selective isolation" means a method by which nucleic acids, derived exclusively or predominantly from the microbial cells contained in the sample, can be made available reproducibly from such a composite sample.

Preferably, the method according to the invention is used for sequential lysis of the cells present in the sample, the higher eukaryotic cells and/or tissues being lysed first, followed in a subsequent step (after removing cell debris and residues of the lysed higher eukaryotic cells and/or tissues) by disintegration of the (prokaryotic or eukaryotic) microbial cells. The nucleic acid obtained in this way can then be isolated by binding and purification by existing methods.

Within the scope of the present invention the terms "microbial cell" or "microorganism" denote a diverse group of organisms, which exist in nature autonomously as a single cell or as a cell cluster, and therefore differ from higher eukaryotic cells (such as animal cells in a tissue, e.g. tissue cells of a mammal), that do not occur in nature as a single cell, but exclusively as constituents of multicellular organisms. According to the invention, the microbial cells can be for example prokaryotic cells, such as bacteria or archaebacteria, or also eukaryotic cells, such as yeasts, lower and higher fungi or protozoa. According to a preferred embodiment the microbial cells are prokaryotic cells. According to a particularly preferred embodiment the prokaryotic cells are bacteria.

Within the scope of the present invention the term "prokaryotic cell" or "prokaryote" means any cell or any organism belonging to the phylogenetic group of the Archaea or Bacteria (cf. Balows, Trüper, Dworkin, Harder, Schleifer: The Procaryotes; Chapter 142, pages 2696-2736 (1992).

Prokaryotic cells have clear differences from eukaryotic cells, which are reflected in structural characteristics of cellular organelles, cell wall and the like. These characteristics are well known to a person skilled in the art. Thus, the terms "microbial cell" or "microorganism" comprise in particular various genera of Gram-positive and Gram-negative bacteria, for example pathogenic bacteria of the genera *Mycobacterium, Enterococcus, Streptococcus, Staphylococcus, Salmonella, Legionella, Clamydia, Shigella, Pseudomonas, Listeria, Yersinia, Corynebacterium, Bordetella, Bacillus, Clostridium, Haemophilus, Helicobacter* and *Vibrio*.

In addition, the microbial cells or microorganisms can, according to the invention, also be eukaryotic cells. According to a preferred embodiment the microbial cells are fungal cells. Fungi whose nucleic acids can be isolated according to the method of the present invention, may comprise in particular pathogenic fungi of the genera *Aspergillus* (e.g. *A. fumigatus, A. niger, A. flavus, A. nidulans*), *Basidiobolus* (e.g. *B. microsporus, B. ranarum*), *Cephalosporium* (e.g. *C. chrysogenum, C. coremioides, C. diospyri, C. gregatum*) and other pathogenic fungi of the genera *Entomophthora, Skopulariopsis, Mucor, Rhizomucor, Absidia, Rhizopus, Altenaria, Stemphylium, Botrytis, Chrysosporium, Curvularia, Helmithosporium, Hemispora, Nigrospora, Paecilomyces, Phoma, Thielavia* or *Syncephalastrum*. Pathogenic yeasts of the genus *Candida*, e.g. *C. albicans, C. guilliermondii, C. kruzei, C. parapsilosis, C. tropicalis* and others are also covered by the invention.

Furthermore, the microbial cells or microorganisms can, according to the invention, also comprise algae, for example *Ceratium massiliense, Dinophysis nitra, Gymnodinium sanguineum, Trachelomonas* spp., *Euglena* spp., *Coscinodiscus* spp., *Eremosphaera, Chlorella, Chlorococcum* or protozoa, for example *Cryptosporidium parvum, Cryptosporidium hominis, Cryptosporidium serpentis, Toxoplasma gondii, Trypanosoma brucei, Trypanosoma cruzei, Plasmodium falciparum, Plasmodium malariae*. In the case of the protozoa, in particular it can be their resting forms, which sometimes have envelope-like shells of proteoglycans.

The term "eukaryotic cell" or "eukaryote" denotes in the present description any cell of unicellular or multicellular organisms belonging to the phylogenetic group of the Eukarya. These cells possess a cell nucleus, which is enclosed by a cell membrane and comprises several DNA molecules, which divide by mitosis. Eukaryotic cells comprise single-celled organisms such as single-celled algae, fungi (e.g. yeasts) or protozoa, which can also live as parasites, commensals or saprophytes at times or permanently in or on a host organism. Furthermore, the cells of multicellular organisms, for example of animal organisms such as mammals, fungi or plants are also classified as eukaryotic cells.

The term "higher eukaryotic cell" means, within the scope of the present invention, a eukaryotic cell of a higher state of development, such as those which occur for example in animal or plant organisms. On the one hand these cells can be cells that are organized in a tissue, i.e. the higher eukaryotic cell does not perform all vital biochemical and metabolic functions independently, but as a rule is specialized for performing one or more functions.

On the other hand the term comprises single cells (e.g. blood cells, spermatozoa), such as those which occur in a liquor of a mammal (e.g. in blood or lymph) or an excreted product of a mammal (e.g. in urine or saliva).

Higher eukaryotic cells comprise inter alia all cells from a mammal, an insect, a mollusk or from a higher plant (e.g. monocotyledons and dicotyledons). "Higher eukaryotic tissue" therefore means, within the scope of the present invention, a collection of higher eukaryotic cells that are organized in a cell aggregate. Examples for higher eukaryotic tissues are for example the organs of mammals (liver, heart, skin, pancreas) or leaf or root tissue of a plant. According to a preferred embodiment of the invention, the higher eukaryotic tissue is from a mammal. According to a particularly preferred embodiment of the invention the higher eukaryotic tissue is from a human.

The term "composite sample" denotes, in the context of the present invention, a sample that comprises at least two different nucleic acid-containing cells (e.g. blood or tissue cells of a mammal, bacterial cells, plant tissue cells or mycelial cells of fungi). Preferably the composite sample is from a natural environment, for example from a human, plant or animal organism. According to a preferred embodiment the composite sample is a blood sample. According to a particularly preferred embodiment the composite sample is a blood sample of a mammal, e.g. of a human. Furthermore, the composite sample can also be blood products, in particular thrombocyte concentrates and erythrocyte concentrates, other body fluids, in particular aspirates (e.g. joints, eyes), liquor and bronchial-alveolar lavage.

Within the scope of the present invention the term "lysis", in connection with cells, generally means any process that leads to the disruption of the outer structure of the cell and its organelles.

Cell lysis (cytolysis) leads to the breakdown of the intact cell and release of the nucleic acid from the respective cellular compartment or organelle (cell nucleus, mitochondria, chloroplasts).

Cytolysis takes place by disruption of the structures (for example membranes and cell wall) that envelope the nucleic acids of the cells and separate them from the surrounding medium. Thus, the deoxyribonucleic acid (DNA) in eukaryotic cells is separated from the surrounding medium by at least the nuclear envelope, cytoplasmic membrane and possibly cell wall or cell-enveloping structures such as peptidoglucans. In bacteria, which do not have a cell nucleus and therefore all the nucleic acids are located in the cytoplasm, the nucleic acids are separated from the surrounding medium by a cytoplasmic membrane and peptidoglycan cell wall and possibly a lipopolysaccharide layer. Both in eukaryotic cells and in prokaryotic cells, in physiological terms lysis leads to cell death. The term "lyse" thus denotes any activity that leads to lysis of cells or tissues.

The method according to the invention comprises steps in which first the higher eukaryotic cells and/or tissues and in a subsequent step also the prokaryotic or eukaryotic microbial cells in the composite sample are lysed. This involves release of the nucleic acids from the respective cells or tissues. Within the scope of the present invention, lysis of higher eukaryotic cells and/or tissues (step a of the method) is carried out in such a way that lysis of the microbial cells present in the sample does not occur.

The latter remain substantially intact, i.e. the outer boundary of these cells (cell wall or similar structures) is not disrupted by the mode of lysis employed in step a) of the method according to the invention, so that no nucleic acids are released from the microbial cells.

In the first step of the method according to the invention for selective purification of nucleic acid from microbial cells, the higher eukaryotic cells and/or tissues contained in the sample are lysed.

During this process, all or at least a considerable proportion of the higher eukaryotic cells and/or tissues present in the sample are lysed. It is preferred to use conditions in the first step of the method that result in more than 30% of the higher eukaryotic cells and/or tissues contained in the sample being lysed, and it is particularly preferred if more than 40%, 50%, 60%, 70%, 80%, 90%, 95% or 99% of the higher eukaryotic cells and/or tissues present in the sample are lysed. In order to determine the proportion of higher eukaryotic cells and/or tissues that are lysed in the selected conditions in the first step of the method according to the invention, control tests can be carried out, which provide quantitative results relating to the lysis of the cells. The extent of lysis of the higher eukaryotic cells and/or tissues under the conditions selected in the first step of the method according to the invention can for example be determined using a quantitative PCR reaction. For this, first the lysis step is performed on an aliquot of a defined sample and the nucleic acid released is purified by existing methods. All of the purified nucleic acid can then be used as the template in a PCR or RT-PCR for the amplification of a gene (e.g. cytochrome B) that is specific for higher eukaryotes.

By comparing with the amplification products from another aliquot of the same sample, which was completely digested by the usual techniques, information can be obtained regarding the extent of lysis in the selected conditions.

The conditions to be applied in the first step of the method are selected in such a way that the microbial cells contained in the composite sample remain intact. This means that the microbial cells present in the sample should only be lysed to a slight extent under the selected conditions.

These selective conditions can for example be provided by means of the concentration of lysing agents (see below). It is preferred that under the selected conditions only a proportion of 15% or less of the microbial cells in the composite sample is lysed. According to a particularly preferred embodiment, the proportion of the lysed microbial cells in the first step is less than 40%, 30%, 20%, 10%, 5%, wherein less than 3% or less than 1% is particularly preferred. The degree of lysis of particular microbial cells in defined lysis conditions can be determined by sufficiently known methods, for example by using a pure culture of the particular organism in the selected lysis conditions and measuring (simultaneously or subsequently) optical density at a wavelength of 260 nm. At this wavelength, nucleic acids display a characteristic absorption maximum, so that the lysis of the cells can be quantified on the basis of the release of nucleic acids from these cells. Alternatively, the PCR techniques described above in connection with the higher eukaryotic cells and/or tissues can also be used.

Methods of lysis are described sufficiently in the state of the art for various cell types and also tissues. Bacterial cells, for example, can be lysed by repeated thawing and freezing, treatment with enzymes such as lysozymes or lysostaphin, mechanical treatment in a French press or cell mill, ultrasonic treatment or similar methods.

Certain eukaryotic cells, for example yeast cells, can be lysed for example by mechanical treatment with glass beads or enzymatic treatment with zymolase (lyticase). Fungal cells can be lysed by mechanical treatment such as trituration under liquid nitrogen or enzymatic treatment with chitinase.

Plant tissues are generally lysed by trituration under liquid nitrogen and enzymatic treatment with proteases.

Various other eukaryotic cells, for example animal cells, can often be lysed by osmolysis in a hypotonic buffer or by means of electrical homogenizers or enzymatic treatment with proteases. Almost any kind of cell or tissue can be lysed by adding certain aggressive chemicals (e.g. chaotropic salts or detergents).

According to a particularly preferred embodiment of the present invention, lysis of the higher eukaryotic cells and/or tissues in the composite sample is carried out by adding a lysing agent. The lysing agent can be a chemical substance (or a mixture of substances) that disrupts the membrane and/or cell wall structure of cells or tissues. The conditions are selected in such a way that the lysing agent is first used at a concentration that leads to lysis of higher eukaryotic cells and tissues, so that the nucleic acids are released from them. The concentration of the particular agent is selected in such a way that the microbial cells (for example bacteria) contained in the same sample are not attacked.

The lysing agent can for example be contained in a solution that is added to the composite sample in question. The solution can also contain other substances, which intensify and/or support the lysing action of the particular agents used.

Preferably the lysing agents are contained in a buffered solution, which can comprise one or more of the following substances: buffers such as TRIS (Tris(hydroxymethyl)-aminomethane), MOPS (3-(N-morpholino)-propanesulfonic acid) or HEPES (N-(2-hydroxyethyl)-piperazine-N'-ethanesulfonic acid), chelating agents such as EDTA (ethylenediamine tetraacetic acid), EGTA (ethyleneglycol-bis(β-aminoethylether)-N,N,N',N'-tetraacetic acid).

According to a particularly preferred embodiment, the lysing agent is one or more chaotropic agents and/or one or more surfactants, i.e. lysis of the cells can be carried out both with one or more chaotropic agents or with one or more surfactants. The chaotropic agents that can be considered for use in the first lysis step can be chaotropic salts, for example guanidine hydrochloride, sodium iodide, guanidine isothiocyanate or mixtures thereof. Guanidine salts can be used up to 4-5 mol/l and surfactants up to 20 wt. %, without microbial cells being lysed (<40%); 1M guanidine salts and 1 wt. % surfactants are preferred (with respect to the use of the endonuclease).

Within the scope of the present invention it was found, surprisingly, that composite samples comprising human blood cells and human cells from vascular tissue on the one hand and bacterial cells on the other hand, can be treated by incubation with chaotropic salts, such as guanidine hydrochloride and guanidine isothiocyanate, in such a way that only the human cells are lysed, but not the bacterial cells. According to a particularly preferred embodiment of the present invention, the lysing agent thus comprises a mixture of the chaotropic salt guanidine hydrochloride and the surfactant Tween-20.

According to a particularly preferred embodiment the lysing agent comprises a mixture of guanidine hydrochloride at a final concentration of 1 mol/l and Tween-20 in an amount of 1 wt. %.

In a subsequent step, the microbial cells that emerged unscathed from the lysis in step a) of the method according to the invention are separated from the lysed higher eukaryotic cells. Methods that are sufficiently known in the state of the art can be employed for the purpose of this separation.

According to one embodiment of the invention, the microbial cells are separated by centrifugation. Customary rotary speeds can be used, that are capable of sedimenting bacterial cells in a suitable centrifuge container, whereas the dissolved constituents of the lysed eukaryotic cells and/or tissues remain in the supernatant. As a rule, said rotary speeds are in the range 1000-15000×g.

According to an alternative embodiment, the microbial cells are separated from the lysed higher eukaryotic cells and/or tissues by filtration. Filtration techniques are well known to a person skilled in the art and comprise for example filtration through filters having a pore size that provides effective separation of smaller cellular constituents, cell debris and liquids from intact microbial cells. Correspondingly suitable filters are for example available from the company Sartorius under the designation Sartobran with pore sizes of 0.2-0.45 μm. The filter materials can, for reasons of simple handling, also be in the form of usual prep-spin columns.

After the microbial cells have been separated from the lysed higher eukaryotic cells and/or tissues, lysis of the microbial cells is carried out (step c of the method according to the invention).

Lysis can be carried out by all methods known to a person skilled in the art that are suitable for lysis of the particular cells. According to a preferred embodiment of the present invention, lysis of the microbial cells is carried out by mechanical methods. Mechanical methods for the disruption of cells are well known and comprise, among others, homogenization by means of a triturator or by means of electrical or mechanical apparatus, for example by ultrasonic treatment, French press, cell mill.

According to a further embodiment of the present invention, the lysis of the microbial cells in step c) of the method according to the invention is carried out enzymatically. In this, depending on the particular organism that is to be detected, an enzyme can be selected that leads to disruption of the cell wall or the outer boundary structure. For example, this can be lysozyme for prokaryotes, lyticase for yeasts, chitinases for fungi, cellulases for algae and proteases for protozoa. If, for example, bacteria with an unusual cell wall structure are to be lysed, consideration can also be given to other enzymes for use within the scope of the method according to the invention, e.g. lysostaphin for dissolving the cell wall of staphylococci. Moreover, proteases can also be used in the lysis of both microbial prokaryotic cells and microbial eukaryotic cells. Of course, the lysis of microbial cells can also be carried out by a method that comprises mechanical and enzymatic treatments. For the lysis of microbial cells it is also possible to use the chaotropic agents and/or surfactants already mentioned above, at concentrations that exceed the concentrations of the agents stated above in the lysis of the higher eukaryotic cells. For example, guanidine hydrochloride or guanidine isothiocyanate can be used at concentrations greater than 4 mol/l or 5 mol/l in the particular reaction batch; in this step, even higher concentrations can be used, up to the limit of solubility of the respective substance.

Moreover, surfactants can also be added to the chaotropic agents. A combination of enzymatic treatment and the use of chaotropic agents and/or surfactants can also be applied within the concentration range used for the lysis of higher eukaryotic cells or tissues, because the cell walls or outer boundary structures of the cell are removed by the enzymatic treatment and cell membranes are disrupted by chaotropic salts and/or surfactants, leading to lysis of the microbial cells.

Finally, purification of the nucleic acids released from microbial cells is carried out. This can be done using methods that are known in the state of the art, for example phenol-chloroform extraction. Alternative methods of purification of nucleic acids have been developed increasingly in recent years, which are characterized by ease of use and reduced health risks (e.g. because solvents such as chloroform or phenol are not used). In these, usually in the presence of high ionic strength (e.g. in the presence of chaotropic salts), the nucleic acids are bound to mineral support materials, for example glass particles, finely ground glass powder, diatomaceous earth or silica gels, washed and finally eluted in a suitable buffer. A nucleic acid purification system of this kind is available commercially in the form of kits, e.g. from Molzym GmbH & Co KG (Bremen, DE), Qiagen (Hilden, DE), Macherey-Nagel (Düren, DE), Roche (Basel, CH) or Sigma (Deisenhofen, DE). Nucleic acid purification systems using chaotropic salts can be used especially advantageously within the scope of the method according to the invention, because after the lysis steps a) and c) the released microbial nucleic acids are already in a high-molar chaotropic environment. However, other systems for nucleic acid purification, which are based on the use of polystyrene beads, nitrocellulose paper etc. as support material, can also be used within the scope of the present invention.

The method of the present invention makes it possible to prepare nucleic acids of microbial cells from composite samples at a purity that ensures the highest possible degree of absence of disturbance in subsequent methods, in particular in diagnostic techniques for detecting particular pathogenic bacteria. It is preferred that the nucleic acid which is isolated from the microbial cells is DNA and/or RNA.

According to the method of the present invention, the composite sample that is investigated can comprise body fluids, for example blood, urine, feces, sputum, lavage, aspirate, wound smear, lymph and/or secretion of human or animal origin and/or tissues of human or animal origin or portions thereof. According to a particularly preferred embodiment, the higher eukaryotic cells that are present in the composite sample comprise blood cells or tissue cells of human or animal origin. According to a particularly preferred embodiment the composite sample can be blood products, in particular thrombocyte concentrates and erythrocyte concentrates, or other body fluids that are isolated within the scope of diagnosis of infection, in particular aspirates (e.g. joints, eyes), liquor and bronchial-alveolar lavage. Furthermore, the composite sample can comprise tissues of plant origin or portions thereof. The sample can comprise tissues from patients infected with bacteria, yeasts, fungi or protozoa, plants or animals infected with pathogenic bacteria or fungi. According to a particularly preferred embodiment the composite sample contains blood from a human or an animal infected with a bacterium. Moreover, there are also symbiotic systems, for example in the case of sponges, which form a close association with bacteria and give rise to analytical and biotechnological questions.

The method according to the invention is furthermore also suitable for the detection of microbial cells or organisms in plant material.

Thus, in particular, plant-pathogenic or plant-colonizing prokaryotic organisms, for example certain species of bacteria of the genus *Mycoplasma, Clavibacter, Xanthomonas, Corynebacterium, Acidovorax, Brenneria, Burkholderia, Rhizobium* or *Agrobacterium*, among others, in composite samples with plant material, can be detected directly. According to a particular embodiment, the composite sample comprises plant material, in particular material from leaf, stem, root, seeds and fruits.

According to a further preferred embodiment, the nucleic acid released from the higher eukaryotic cells is removed from the sample following lysis of the eukaryotic cells in step a).

This can be done for example using conventional filtration methods that are sufficiently known in the state of the art. For example, the nucleic acid can be removed from the sample with the aid of the usual kits for nucleic acid purification. For this it is possible to use the same kits that are then used for purification of the nucleic acids from the prokaryotic cells. Thus, according to a particular aspect, the present invention also relates to a method for the sequential isolation of nucleic acid from higher eukaryotic and microbial cells, in which first the nucleic acids from higher eukaryotic cells are released and purified, and in a subsequent step the nucleic acids from microbial cells are released and purified.

If there is no further use for the higher eukaryotic nucleic acids, these can also be removed from the sample by degrading it.

This is advantageous in particular in subsequent applications of the respective target nucleic acid that require a high purity of the target nucleic acid and consequently quantitative removal of other nucleic acids as far as possible (e.g. PCR). Said degradation is preferably carried out by enzymatic treatment of the sample with a DNA-degrading nuclease as described above. The nuclease can be added right at the start of lysis of the higher eukaryotic cells (e.g. simultaneously with addition of the lysing substances to the sample) or can be added after completion of lysis (i.e. after an incubation phase).

The nuclease can be an endonuclease or an exonuclease. Preferably, it is an endonuclease. Especially preferably, it is one of the endonucleases defined above from *Escherichia coli, Vibrio cholerae, Erwinia* chrysanthemi or *Aeromonas hydrophila*.

Thus, according to a preferred embodiment, the nuclease can have the amino acid sequence shown in SEQ ID NO:1, SEQ ID NO:2, SEQ ID NO:3 or SEQ ID NO:4, also including the variants and derivatives of the polypeptides and enzymatically active fragments of the polypeptides and variants thereof that are defined above.

The present invention also provides a kit for carrying out a method for the isolation and/or purification of RNA using a DNA-degrading nuclease, which is capable of degrading DNA in the presence of one or more chaotropic agents and/or one or more surfactants. Said kit comprises a DNA-degrading nuclease that is capable of degrading DNA in the presence of one or more chaotropic agents and/or one or more surfactants. The kit further comprises buffers and reagents that are suitable for the isolation and/or purification of RNA.

According to a preferred embodiment, the nuclease comprises the polypeptide shown in SEQ ID NO:1, SEQ ID NO:2, SEQ ID NO:3 or SEQ ID NO:4. The invention further relates to the use of a kit comprising a DNA-degrading nuclease that is capable of degrading DNA in the presence of one or more chaotropic agents and/or one or more surfactants, for the isolation and/or purification of RNA.

The present invention also provides a kit for carrying out a method for the isolation of nucleic acid from microbial cells that are present in a composite sample that comprises higher eukaryotic cells and/or tissues. According to a particular embodiment, said kit comprises a DNA-degrading nuclease that is capable of degrading DNA in the presence of one or more chaotropic agents and/or one or more surfactants.

The invention is described in the following on the basis of examples, for the purpose of illustration, without limiting the invention. It will be evident to a person skilled in the art that modifications and variations of the examples described are possible without deviating from the idea of the invention.

EXAMPLES

A. Characteristics of Endonuclease I from *E. coli*

Figure 3:
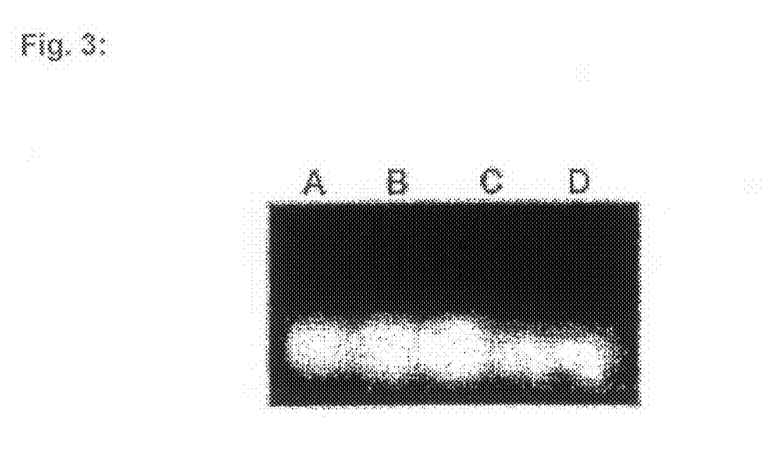
FIG. 3: Test (in duplicate) for RNase activity of endonuclease I from *E. coli* with yeast-RNA (50 μg/test, 16 h incubation). A: control RNA without incubation; B, C: RNA without or with 2 units of endonuclease I from *E. coli* (37° C.); D, E: as B/C but at 55° C.
Figure 4:
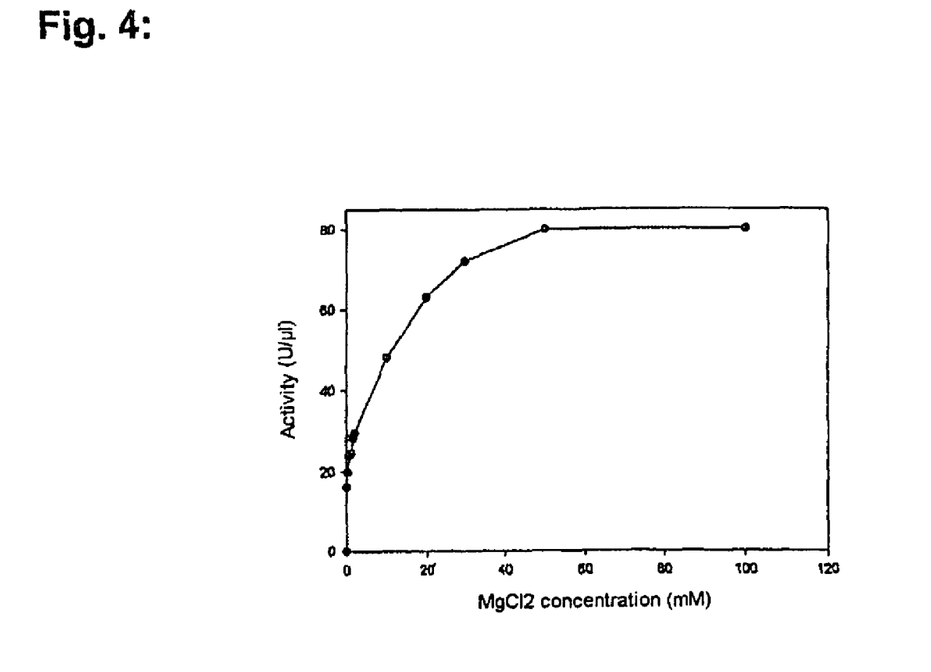
FIG. 4: Enzymatic activity of endonuclease I from *E. coli* as a function of magnesium chloride concentration.
Figure 5:
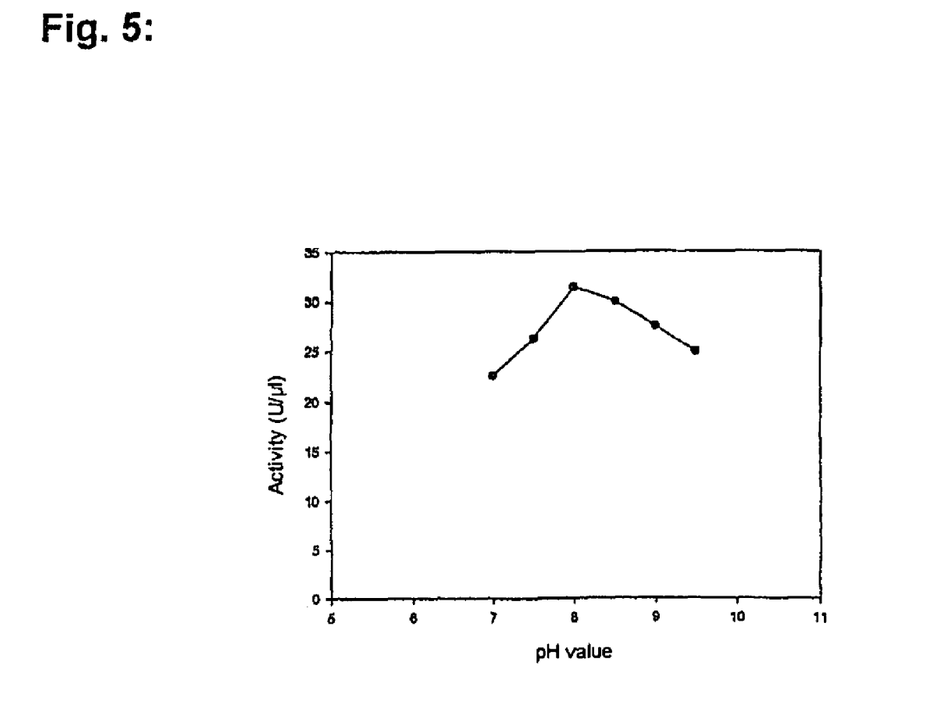
FIG. 5: Enzymatic activity of endonuclease I from *E. coli* as a function of the pH value.
Figure 6:
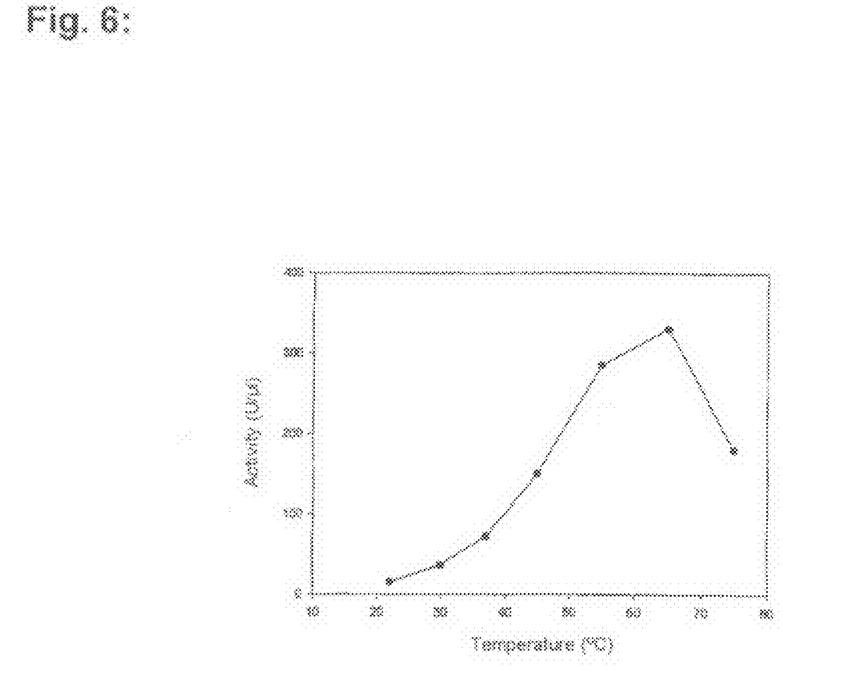
FIG. 6: Enzymatic activity of endonuclease I as a function of temperature. Endonuclease I is a thermophilic enzyme (optimum at 65° C.).
Figure 7:
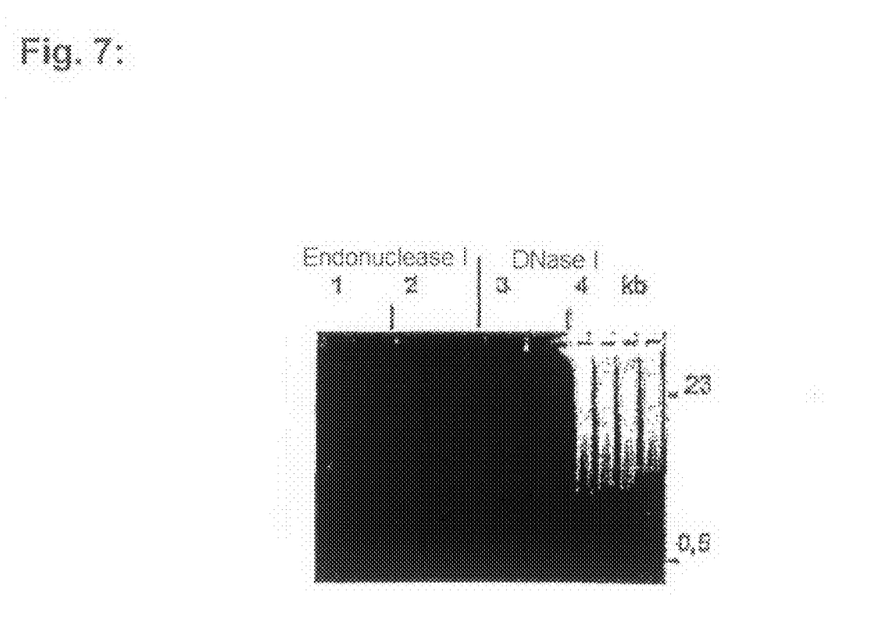
FIG. 7: Incubation of calf thymus DNA (5 μg) with 200 units endonuclease I or 1000 U pancreatic DNase I in the presence of 1 mol/l guanidine-HCl (lanes 1, 3) or 1 mol/l guanidine isothiocyanate (lanes 2, 4). It can be seen that endonuclease I degrades DNA completely in both conditions (lanes 1, 2), whereas DNase I has only slight activity (lane 3, see bands at 0.5 kb) or no longer any activity (lane 4).
Figure 8:
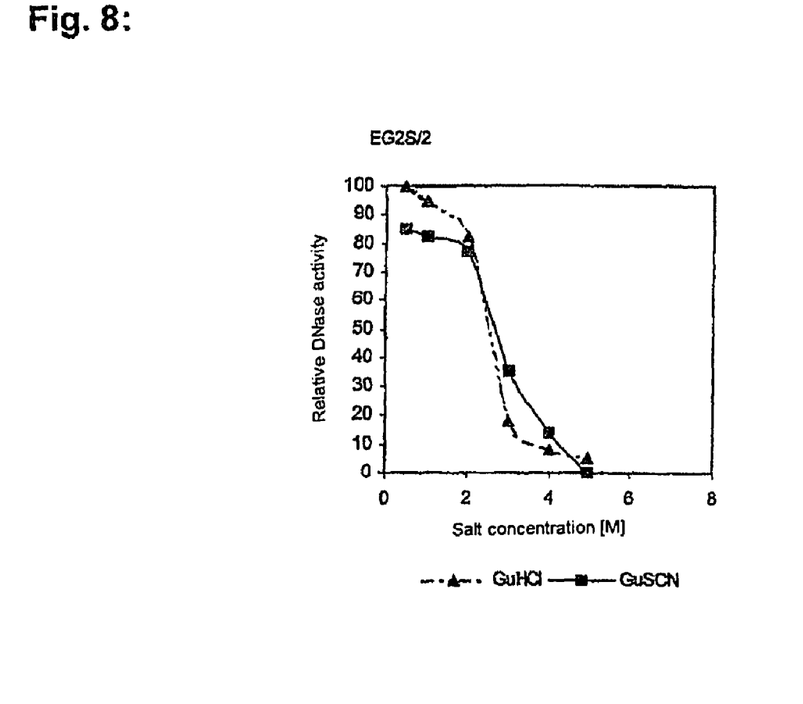
FIG. 8: Guanidine salt resistance of DNase from EG2S/2 (*Halobacillus* sp.). With 2 M guanidine hydrochloride and guanidine isothiocyanate, the activity of the enzyme is still approx. 80% of the activity without guanidine salts. 80% of the DNase activity of SJ1/4 was still present even with 4 M guanidine isothiocyanate or 5 M guanidine hydrochloride. 100% corresponds to approx. 30 units of enzyme in the assay. GuHCl (guanidine hydrochloride), GuSCN (guanidine isothiocyanate).
Figure 9:
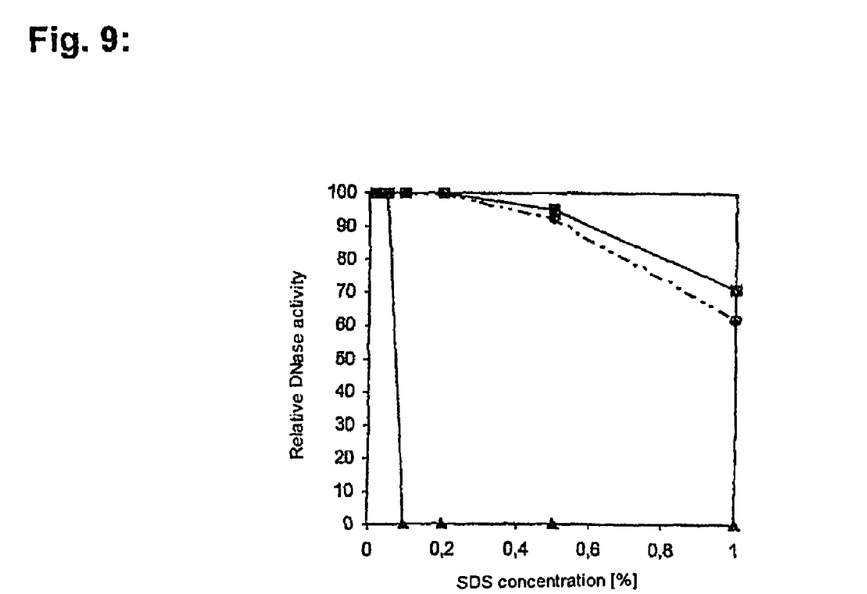
FIG. 9: DNase activities of SJ1/4 (circles), EG2S/2 (squares) and Merck Benzonase (triangles) in the presence of SDS. 100% corresponds to approx. 30 units enzyme. The sensitivity of the commercial Benzonase can clearly be seen, whereas the isolates still possess 60-70% activity at 1% SDS.

The general biochemical characteristics of endonuclease I from *E. coli* (SEQ ID NO:1) were investigated. The enzyme possesses chaotropic-resistant properties (guanidine hydrochloride or guanidine isothiocyanate). It exhibits endonuclease activity without RNase activity (see FIG. 3). Magnesium ions are required as cofactor at an optimum of 50 mmol/l (see FIG. 4). The optimum pH of the enzyme is pH 8.0 (see FIG. 5). The optimum temperature of the enzyme is 65° C. (see FIG. 6). Compared with common, commercially available endonucleases (e.g. DNase I, from Roche, Basel, CH and Benzonase, Merck, Darmstadt), the endonuclease is far more resistant to chaotropic conditions such as 1 mol/l guanidine hydrochloride or 1 mol/l guanidine isothiocyanate (see FIG. 7).

B. Nucleic Acid Purification

The following materials were used for the nucleic acid purification tests presented below:
Buffer 1 (5 mol/l guanidine hydrochloride, 5% Tween-20, 50 mmol/l Tris-HCl, pH 8.0);
Buffer 2 (0.3 mol/l $MgCl_2$, 50 mmol/l Tris-HCl, pH 8);
Buffer 3 (5 mol/l guanidine isothiocyanate, 5% Tween-20 (v/v), 50 mmol/l Tris-HCl, pH 8);
Buffer 4 (50 mmol/l Tris-Cl, pH 8, 10 mmol/l EDTA, pH 8.0);
Buffer 5 (50 mmol/l Tris-Cl, pH 8.0, 10 mmol/l EDTA, pH 8.0, 20% (w/v) sucrose);
Buffer 6 (50 mmol/l Tris-Cl, pH 8.0, 10 mmol/l EDTA, pH 8.0, 6.2 mmol/l $CaCl_2$, 1.25% (w/v) sodium dodecyl sulfate) New
Lysozyme (100 mg/ml; >100 000 U/mg; available from Molzym GmbH & Co KG, Bremen, Germany);
Endonuclease I from *Escherichia coli*; SEQ ID NO:1 (500 U/µl; available from Molzym GmbH & Co KG, Bremen, Germany).

Procedure:
1. 10 ml fresh whole blood (stabilized with EDTA, heparin or citrate) or concentrates of processed blood, including thrombocyte or erythrocyte concentrates, to which bacteria or natural samples had been added, were pipetted into a sterile 50-ml Falcon tube, and 3.5 ml of buffer 1 was added. It was mixed with a Vortexer at full speed for 5 seconds and left to stand for 5 to 10 minutes.
2. 3.5 ml of buffer 2 and 10 µl of Endonuclease I (500 U/µl) were added to the lysate, optionally briefly mixing the buffer and the enzyme before use. Then it was mixed immediately for 5 seconds (Vortexer). It was left to stand for 15 minutes, the temperature being 20 to 25° C.
3. The bacterial cells were harvested by centrifuging for 10 minutes in a high-speed centrifuge at 11 000×g. Then the supernatant was removed by decanting.
4. In the next step, 1 ml of buffer 4 was added, mixed (Vortexer) until the sediment was resuspended, and the suspension was transferred to a sterile 1.5 or 2 ml polypropylene tube. By centrifuging at the highest speed (>13 000 rpm) for 10 minutes, the bacterial cells were caused to sediment. The supernatant was removed carefully using a pipette. It was found that in many cases the sediment was barely visible. The sample was stirred vigorously (Vortexer) for 10 to 20 seconds.

In many cases it turned out that the pellet consisted of blood cell fragments and bacterial cells, necessitating difficult and costly resuspension. In this case it was stirred with the tip of a pipette and pipetting was carried out several times until a homogeneous suspension was obtained. This washing was for the purpose of removing residues of the chaotropic agent and makes enzymatic treatment possible, as part of nucleic acid extraction from the pellet (see below).

5. The pellet was resuspended in 90 µl of buffer 5 by repeated pipetting. Small particles in the suspension could be ignored, as they dissolved during the enzymatic treatments, in particular in proteinase K digestion (see below).
6. Next, the tube was heated for 5 minutes at 80° C., in order to inactivate Endonuclease I, and was then left to cool to room temperature.
7. 10 µl of lysozyme (or some other enzyme for cell wall degradation such as mutanolysine or lysostaphin) was added and the tube was incubated for 45 min at 45° C.
8. 10 µl of proteinase K and 150 µl of buffer 6 were added. It was stirred with a Vortexer at the highest speed for 5 seconds and incubated for 30 minutes at 45° C.
9. 250 µl of buffer 3 was added, it was stirred using a Vortexer at the highest speed for 5 seconds, and then left to stand for 5 minutes at room temperature. Lysis of the cells occurred, and the protein was denatured.

DNA purification was carried out with a commercial DNA purification kit (PrestoSpin D Bug Kit, Molzym, Bremen, Germany) according to the manufacturer's instructions.

1. Sample Preparation:

The following samples were used for the subsequent isolation processes. A 200-µl aliquot of a whole blood sample of human origin was placed in a 1.5-ml plastic centrifuge tube, 1 µl of a bacterial suspension (approx. $1 \times 10^9$ to $4 \times 10^9$ cells/ml) was added and it was mixed for 5 s using a Vortexer ("spiked whole blood"). Another 200-µl aliquot of the same whole blood sample without bacteria ("unspiked whole blood") was used for purposes of comparison. In addition, by adding 1 µl of a cell suspension with a concentration of approx. $1 \times 10^9$ to $4 \times 10^9$ cells per ml to 200-µl of buffer 4, another comparative sample was prepared ("pure culture"). Furthermore, 200-µl samples of septic blood samples, aspirates (e.g. joints, eyes, pus) and blood products such as thrombocyte concentrates and erythrocyte concentrates, spiked or natural, were used for the next protocol.

2. Isolation Technique

50 µl of buffer 1 was added to each of the samples ("spiked whole blood"; "unspiked whole blood" and "pure culture"), and the samples were stirred for 5 s using a Vortexer. To achieve optimal lysis of blood cells, the samples were left to stand for 5 min.

Then 50 µl of buffer 2 and 1 µl of Endonuclease I were added, stirred for 5 s using a Vortexer and incubated for 15 min at room temperature (20-25° C.). In this way the human DNA was degraded.

Centrifugation was carried out at >13 000 rpm, the sample supernatant was decanted and residues of the fluid were pipetted off and discarded.

Then 400 µl of buffer 4 was added, stirred for 10 s using a Vortexer and centrifuged for 5 to 10 min at 13 000 rpm, to sediment the cells. The supernatant was decanted, and the residues of the fluid were pipetted off and discarded.

After adding 50 µl buffer 4 and 5 µl lysozyme solution to the pellets, the latter were resuspended completely by stirring with the tip of the pipette and by aspirating and discharging. Then the cell suspensions were incubated for 15 min at 37° C. Next, 250 µl of buffer 3 was added and after stirring for 5 s (Vortexer) the samples were left to stand for 5 min, for optimal lysis of the bacterial cells and inactivation of residues of Endonuclease I.

3. Purification of the Bacterial DNA:

The DNA was purified with a commercial DNA purification kit (PrestoSpin D Bug Kit, Molzym, Bremen, Germany) according to the manufacturer's instructions.

For this purpose, first 200 µl of buffer AB was added to the samples and stirred for 5 s (Vortexer). Then the contents of the respective sample tubes were in each case decanted in a spin column and centrifuged for 30 s at >13 000 rpm. The run-through was discarded in each case. The columns were washed by adding 400 µl of buffer WB and then centrifuged for 30 s at >13 000 rpm. The run-through was discarded again.

The columns were washed with 400 µl of 70% ethanol and then dried (3 min, >13 000 rpm).

Next, the spin columns were carefully inserted in sterilized (autoclaved and dried) 1.5-ml plastic centrifuge tubes. 100 µl of buffer EB (70° C.) was in each case pipetted onto the surface of the filter and the cover was closed.

After incubation for one minute, the DNA solution was eluted by centrifugation at >13 000 rpm.

The DNA purified in this way was then analyzed by gel electrophoresis. In order to clarify the advantages of the method according to the invention, for purposes of comparison in each case an aliquot of the samples described in section 1 ("spiked, whole blood", "unspiked whole blood" and "pure culture") was treated using a commercial kit (DNeasy, Qiagen, Hilden, DE) according to the conventional principle of total extraction.

Figure 1:
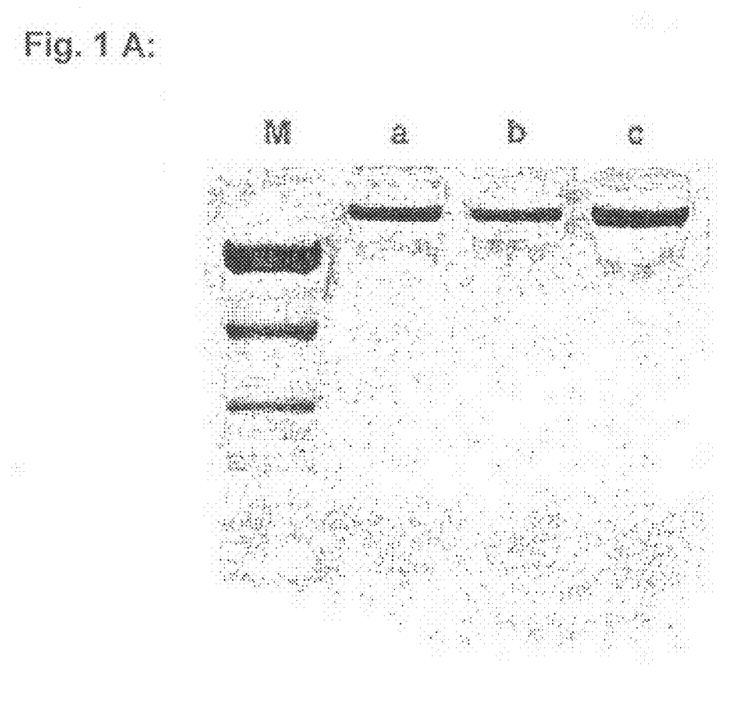
FIG. 1: Electrophoretic separation of extracted DNA; A: DNA from extraction using a commercially available kit for nucleic acid purification (principle of total extraction); B: DNA from extraction by the method according to the invention, a: pure culture; b: unspiked whole blood; c: spiked whole blood.

4. Gel Electrophoresis:

The results of separation by gel electrophoresis are shown in FIGS. 1A and 1B. FIG. 1A shows the result of gel-electrophoretic separation of the nucleic acids from samples that had been isolated using the commercial kit according to the principle of total extraction. It can be seen that this method leads to lysis of the bacterial cells and of the blood cells, the DNA being released from both types of cells.

FIG. 1B shows the result of electrophoretic separation of the nucleic acids from samples that had been treated using the method according to the invention. After lysis of the blood cells, endonuclease I was added for degrading DNA. It can be seen that the DNA of the blood cells is degraded completely. The high-molecular DNA released from lysed bacteria at a later time is obtained from the composite sample in amounts and of a quality (high-molecular) that correspond to the amounts and the quality in the control (compare lanes of the "spiked whole blood" and "pure culture" samples).

5. PCR Amplification

The nucleic acids isolated by the method according to the invention or using conventional kits, which had in each case been purified starting from a composite sample of bacteria and blood ("spiked whole blood"), were used in the following for PCR under the conditions stated below.

PCR was carried out according to regular methods for the amplification of 16S rDNA sequences (25 µl PCR reaction batch; cycles: 5 minutes denaturing at 95° C., followed by 30 cycles of 1 minute denaturing at 95° C., 1 minute annealing at 55° C. and 1 minute extension at 72° C.). The primers used were e.g. 341f (SEQ ID NO:5; 5'-CCT ACG GGA GGC AGC AG-3') and 985r (SEQ ID NO:6; 5'-GTA AGG TTC TTC GCG TT-3').

Figure 2:
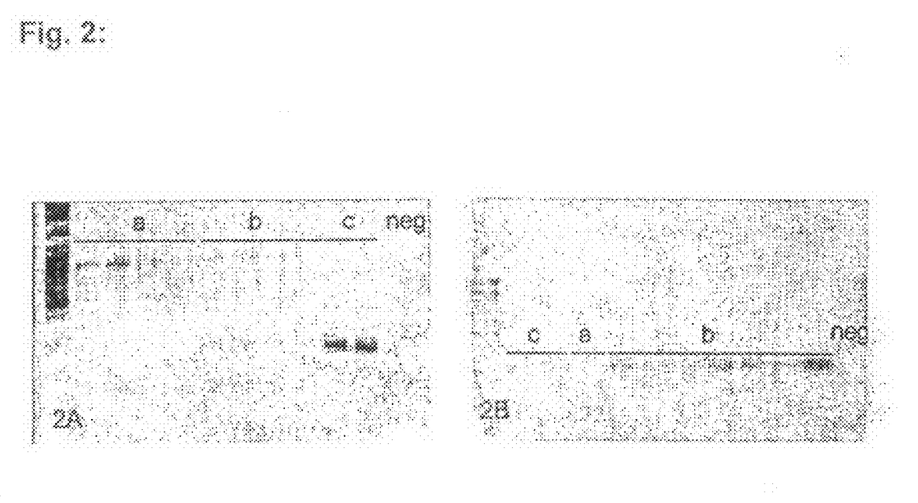
FIG. 2: A: PCR amplification of the 16s-rRNA gene with DNA from composite-sample extracts; A: DNA from extraction using a commercially available kit for nucleic acid purification (principle of total extraction); B: DNA from extraction by the method according to the invention. a: unspiked whole blood; b: spiked whole blood; c: pure culture.

In contrast, FIG. 2A shows the result of PCR using nucleic acids that were obtained using conventional kits. The nonspecific products that arose in the course of amplification in samples that contained human blood cells ("unspiked" and "spike") can be seen clearly.

FIG. 2B shows the result of PCR using nucleic acids that had been isolated using the method according to the invention. It is clear that only one specific band can be seen for the 16S-rRNA product in the samples that contained the bacteria (namely in the sample "spike": corresponds to "spiked whole blood"; and in the sample "pure culture"). The whole blood without addition of bacteria did not have this band.

This shows that using the method according to the invention, the blood cells were disrupted selectively and their nucleic acids were released and were degraded by the nuclease.

The bacterial cells, in contrast, remain intact during this treatment and are not disrupted until the next step, in which their nucleic acids are also released. In the present example, the guanidine isothiocyanate concentration in buffer 3 is high enough to cause inactivation of endonuclease I.

C. Isolation of DNase-Producing Microorganisms from Extreme Habitats

As a method for isolating nuclease-producing microorganisms (Bacteria and Archaea), that are suitable within the scope of the present invention, water and sediment samples were collected from salt-containing (>1% NaCl to 34% [saturation]) and alkaline (pH>7 to 10) locations, e.g. dried-up sea-water puddles or sea water. The samples were plated on agar-containing media according to known microbiological techniques (e.g. shaking up the sediment samples or sea water and application on agar medium, see below). The composition of the media corresponded to published recipes (e.g. Can. J. Microbiol. 6: 165, 1960) or was based on the locally prevailing ion compositions and pH values determined in the physicochemical analysis. A base medium (SML) with the following composition was used successfully as a special embodiment: 7.5 g/l Casamino acids (Difco, Mich.), 10 g/l yeast extract (Difco, Mich.), 11.6 g/l trisodium citrate (Merck, Darmstadt), 0.13 mM magnesium sulfate (Merck, Darmstadt), 0.05 mM calcium chloride (Merck, Darmstadt), 28 mM potassium chloride (Merck, Darmstadt), 0.18 mM iron-II chloride (Merck, Darmstadt) and 10 mM disodium hydrogen phosphate (Merck, Darmstadt). 15 g/l agar (Difco, Mich.) was added to the base medium to consolidate it. The pH value, corresponding to the data measured in situ, was adjusted with 2 M NaOH to values between pH 8.0 and 9.5 or buffered with 75 mM glycine (Merck, Darmstadt) (pH 9.5).

The medium was then autoclaved by the usual method (20-30 min, 120° C., 1 bar excess pressure). According to the salinities measured at the sampling site, commercially available table salt, which had been dry-sterilized for 3 hours at 180° C., was added to the medium at concentrations from 2.9 to 30%. Before pouring into Petri dishes, the table salt was added to the agar base medium and dissolved (SML-agar).

Pure cultures (strains) were obtained by isolating the colonies that developed after a few days up to two weeks after plating of sample material, according to known microbiological methods by several repeated plating on media according to the above composition.

To detect nucleases formed extracellularly (RNases and/or DNases) the strains isolated were plated on SML-agar and adjusted salt concentrations, which additionally contained
a) for the detection of DNases, salmon sperm DNA (0.5 g/l; ICN Biochemicals) and 50 mg/ml Methyl Green (ICN Biochemicals) or
b) for the detection of RNases type VI Torula Yeast RNA (ICN Biochemicals).

The corresponding enzyme activities were visualized by discolored haloes around the colonies (DNases) or clear haloes after overlaying the agar plate with 10% hydrochloric acid solution (RNases).

In the manner described above, 1000 isolates were obtained from the saline sites, including some that displayed nuclease activity (Table 1).

TABLE 1

Properties of selected isolates from saline sites

| Strain designation | Genus (16S rRNA) | Isolation conditions % NaCl/pH | Growth range % NaCl | Optimum growth % NaCl | DNase | RNase |
|---|---|---|---|---|---|---|
| SJ5Ü/4 | *Salinivibrio* sp. | 12/8 | 2.9-12 | 2.9-12 | + | + |
| SJ5S/6 | unknown | 12/8 | 0.5-20 | 12 | + | + |
| EG2S/2 | *Halobacillus* sp. | 12/8 | 0.5-20 | 2.9 | + | + |
| SJ1/4 | unknown | 12/8 | 12-20 | 20 | + | − |
| SJ6/2 | *Halomonas* sp. | 12/8 | 2.9-12 | 2.9 | + | − |
| EG2S/11 | *Deleya* sp. | 12/9.5 | 2.9-12 | 12 | + | − |
| EG2S/14 | *Deleya* sp. | 12/9.5 | 2.9-12 | 12 | + | − |
| SJ6S/18 | *Salinivibrio* sp. | 12/9.5 | 2.9-12 | 2.9-12 | + | + |
| SJ6Ü/21 | unknown | 12/8 | 2.9-12 | 12 | + | + |

Table 1 shows that a broad spectrum of species that form nucleases could be isolated. The strains possess either DNase and RNase activity or only one of the two activities (in Table 1 only DNase; other strains possess only RNase activity, not shown). These nucleases were sometimes active at very high salt concentrations, and thus under chaotropic conditions (e.g. SJ1/4 only with DNase activity at 12-20% NaCl).

The DNases of strains SJ1/4 (unknown, new species; Table 1) and EG2S/2 (*Halobacillus* sp., Table 1) should be described here as being representative of the nucleases of the other strains with respect to resistance to chaotropic conditions.

The invention claimed is:

1. A method for the selective isolation of nucleic acid from microbial cells that are present in a composite sample which comprises higher eukaryotic cells and/or tissues, comprising the steps of
   (a) lysing only the higher eukaryotic cells and/or tissues, wherein the microbial cells remain intact; wherein said lysis is carried out by adding one or more chaotropic agents;
   (b) adding a nuclease capable of degrading DNA in the presence of one or more chaotropic agents;
   (c) separating the microbial cells from the lysed higher eukaryotic cells and/or tissues;
   (d) lysing the microbial cells, so that the nucleic acids are released from these cells;
   (e) isolating the nucleic acids released in step (d).

2. The method of claim 1, wherein the DNA-degrading nuclease has the amino acid sequence shown in SEQ ID NO:1, SEQ ID NO:2, SEQ ID NO:3 or SEQ ID NO:4.

3. The method of claim 1, wherein the DNA-degrading nuclease has the amino acid sequence shown in SEQ ID NO:1.

4. The method as claimed in claim 1, wherein the chaotropic agents are chaotropic salts.

5. The method of claim 4, wherein the chaotropic salts are guanidine hydrochloride, sodium iodide, guanidine isothiocyanate, sodium perchlorate and/or urea.

6. The method of claim 1, wherein the nucleic acid that is to be isolated from microbial cells is DNA.

7. The method of claim 1, wherein the nucleic acid that is to be isolated from microbial cells is RNA.

8. The method of claim 1, wherein the separation in step b) is carried out by centrifugation.

9. The method of claim 1, wherein the separation in step b) is carried out by filtration.

10. The method of claim 1, wherein the lysis of the microbial cells in step d) is carried out by mechanical methods.

11. The method of claim 1, wherein the lysis of the microbial cells in step d) is carried out enzymatically.

12. The method of claim 1, wherein the lysis of the microbial cells in step d) is carried out by adding one or more chaotropic agents.

13. The method of claim 12, wherein the chaotropic agents are guanidine hydrochloride, guanidine isothiocyanate and/or sodium iodide.

14. The method of claim 12, wherein the lysis in step (d) is carried out by further adding one or more surfactants.

15. The method of claim 1, wherein the composite sample comprises blood, blood product, urine, feces, sputum, lavage, aspirate, wound smear, liquor and bronchial-alveolar lavage, lymph and/or secretion of human or animal origin and/or tissues of human or animal origin or portions thereof.

16. The method of claim 15, wherein the blood product is thrombocyte concentrate or erythrocyte concentrate.

17. The method of claim 1, wherein the higher eukaryotic cells are blood cells or tissue cells of human or animal origin.

18. The method of claim 1, wherein the higher eukaryotic cells are plant cells.

19. The method of claim 18, wherein the plant cells comprise material from leaf, stem or root of the plant.

20. The method of claim 1, wherein the lysis in a step (a) is carried out by further adding one or more surfactants.

21. The method of claim 14, wherein the surfactants are sodium dodecyl sulfate, Brji40, Triton X-100 and/or Tween-20.

* * * * *

SEQUENCE LISTING

```
<160> NUMBER OF SEQ ID NOS: 6

<210> SEQ ID NO 1
<211> LENGTH: 235
<212> TYPE: PRT
<213> ORGANISM: Escherichia coli
<220> FEATURE:
<223> OTHER INFORMATION: DNA-specific endonuclease I from Escherichia
      coli K12

<400> SEQUENCE: 1

Met Tyr Arg Tyr Leu Ser Ile Ala Ala Val Val Leu Ser Ala Ala Phe
1               5                   10                  15

Ser Gly Pro Ala Leu Ala Glu Gly Ile Asn Ser Phe Ser Gln Ala Lys
            20                  25                  30

Ala Ala Ala Val Lys Val His Ala Asp Ala Pro Gly Thr Phe Tyr Cys
        35                  40                  45

Gly Cys Lys Ile Asn Trp Gln Gly Lys Lys Gly Val Val Asp Leu Gln
    50                  55                  60
```

```
Ser Cys Gly Tyr Gln Val Arg Lys Asn Glu Asn Arg Ala Ser Arg Val
 65                  70                  75                  80

Glu Trp Glu His Val Val Pro Ala Trp Gln Phe Gly His Gln Arg Gln
                 85                  90                  95

Cys Trp Gln Asp Gly Gly Arg Lys Asn Cys Ala Lys Asp Pro Val Tyr
                100                 105                 110

Arg Lys Met Glu Ser Asp Met His Asn Leu Gln Pro Ser Val Gly Glu
            115                 120                 125

Val Asn Gly Asp Arg Gly Asn Phe Met Tyr Ser Gln Trp Asn Gly Gly
130                 135                 140

Glu Gly Gln Tyr Gly Gln Cys Ala Met Lys Val Asp Phe Lys Glu Lys
145                 150                 155                 160

Ala Ala Glu Pro Pro Ala Arg Ala Arg Gly Ala Ile Ala Arg Thr Tyr
                165                 170                 175

Phe Tyr Met Arg Asp Gln Tyr Asn Leu Thr Leu Ser Arg Gln Gln Thr
            180                 185                 190

Gln Leu Phe Asn Ala Trp Asn Lys Met Tyr Pro Val Thr Asp Trp Glu
        195                 200                 205

Cys Glu Arg Asp Glu Arg Ile Ala Lys Val Gln Gly Asn His Asn Pro
210                 215                 220

Tyr Val Gln Arg Ala Cys Gln Ala Arg Lys Ser
225                 230                 235

<210> SEQ ID NO 2
<211> LENGTH: 230
<212> TYPE: PRT
<213> ORGANISM: Vibrio cholerae
<220> FEATURE:
<223> OTHER INFORMATION: Nuclease from Vibrio cholerae

<400> SEQUENCE: 2

Met Met Ile Phe Arg Phe Val Thr Thr Leu Ala Ala Ser Leu Pro Leu
  1               5                  10                  15

Leu Thr Phe Ala Ala Pro Ile Ser Phe Ser His Ala Lys Asn Glu Ala
                 20                  25                  30

Val Lys Ile Tyr Arg Asp His Pro Val Ser Phe Tyr Cys Gly Cys Glu
             35                  40                  45

Ile Pro Trp Gln Gly Lys Lys Gly Ile Pro Asp Leu Glu Ser Cys Gly
         50                  55                  60

Tyr Gln Val Arg Lys Asn Glu Asn Arg Ala Ser Arg Ile Glu Trp Glu
 65                  70                  75                  80

His Val Val Pro Ala Trp Gln Phe Gly His Gln Leu Gln Cys Trp Gln
                 85                  90                  95

Gln Gly Gly Arg Lys Asn Cys Thr Arg Thr Ser Pro Glu Phe Asn Gln
                100                 105                 110

Met Glu Ala Asp Leu His Asn Leu Thr Pro Ala Ile Gly Glu Val Asn
            115                 120                 125

Gly Asp Arg Ser Asn Phe Ser Phe Ser Gln Trp Asn Gly Val Asp Gly
130                 135                 140

Val Thr Tyr Gly Gln Cys Glu Met Gln Val Asn Phe Lys Glu Arg Thr
145                 150                 155                 160

Ala Met Ala Gln Ser Val Gln Arg Ala Ile Ala Arg Thr Tyr Leu Tyr
                165                 170                 175

Met Ser Glu Gln Tyr Gly Leu Arg Leu Ser Lys Ala Gln Thr Gln Leu
            180                 185                 190
```

```
Met Gln Ala Trp Asn Asn Gln Tyr Pro Val Ser Glu Trp Glu Cys Val
        195                 200                 205

Arg Asp Gln Arg Ile Glu Lys Val Gln Gly Asn Ser Asn Leu Leu Cys
        210                 215                 220

Ala Cys Lys Cys Pro Asn
225                 230

<210> SEQ ID NO 3
<211> LENGTH: 266
<212> TYPE: PRT
<213> ORGANISM: Erwinia chrysanthemi
<220> FEATURE:
<223> OTHER INFORMATION: Nuclease from Erwinia chrysanthemi

<400> SEQUENCE: 3

Met Leu Arg Asn Leu Val Ile Phe Ala Val Leu Gly Ala Gly Leu Thr
1               5                   10                  15

Thr Leu Ala Ala Ala Gly Gln Asp Ile Asn Asn Phe Thr Gln Ala Lys
            20                  25                  30

Ala Ala Ala Lys Ile His Gln Asp Ala Pro Gly Thr Phe Tyr Cys
        35                  40                  45

Gly Cys Lys Ile Asn Trp Gln Gly Lys Lys Gly Thr Pro Asp Leu Ala
    50                  55                  60

Ser Cys Gly Tyr Gln Val Arg Lys Asp Ala Asn Arg Ala Ser Arg Ile
65                  70                  75                  80

Glu Trp Glu His Val Val Pro Ala Trp Gln Phe Gly His Gln Arg Gln
                85                  90                  95

Cys Trp Gln Asp Gly Gly Arg Lys Asn Cys Thr Lys Asp Asp Val Tyr
            100                 105                 110

Arg Gln Ile Glu Thr Asp Leu His Asn Leu Gln Pro Ala Ile Gly Glu
        115                 120                 125

Val Asn Gly Asp Arg Gly Asn Phe Met Tyr Ser Gln Trp Asn Gly Gly
    130                 135                 140

Glu Arg Gln Tyr Gly Gln Cys Glu Met Lys Ile Asp Phe Lys Ser Gln
145                 150                 155                 160

Leu Ala Glu Pro Pro Glu Arg Ala Arg Gly Ala Ile Ala Arg Thr Tyr
                165                 170                 175

Phe Tyr Met Arg Asp Arg Tyr Asn Leu Asn Leu Ser Arg Gln Gln Thr
            180                 185                 190

Gln Leu Phe Asp Ala Trp Asn Lys Gln Tyr Pro Ala Thr Thr Trp Glu
        195                 200                 205

Cys Thr Arg Glu Lys Arg Ile Ala Ala Val Gln Gly Asn His Asn Pro
    210                 215                 220

Tyr Val Gln Gln Ala Cys Ser Pro Asp Ala Pro Tyr Tyr Asn Gly
225                 230                 235                 240

Leu Ser Leu Ile Met Ile Ala Ala Val Ala Thr Val Ala Ala Arg Trp
                245                 250                 255

Leu Thr Pro Ala Gly His Leu Pro Ser Asp
            260                 265

<210> SEQ ID NO 4
<211> LENGTH: 230
<212> TYPE: PRT
<213> ORGANISM: Aeromonas hydrophila
```

```
<220> FEATURE:
<223> OTHER INFORMATION: Nuclease from Aeromonas hydrophila

<400> SEQUENCE: 4

Met Phe Arg Pro Leu Leu Ser Leu Cys Leu Ala Leu Leu Val Ser Ala
1               5                   10                  15

Pro Ala His Ala Asp Asn Ile Gln Thr Phe Arg Ala Ala Lys Gln Asp
            20                  25                  30

Leu Asn Lys Leu Tyr Gln Ser His Pro Val Thr Phe Tyr Cys Gly Cys
        35                  40                  45

Asn Ile Lys Phe Ser Gly Lys Lys Met Ala Pro Asp Trp Glu Ser Cys
50                  55                  60

Gly Tyr Leu Pro Gly Lys Gln Ala Glu Arg Ala Ser Arg Ile Glu Trp
65                  70                  75                  80

Glu His Val Val Pro Ala Trp Glu Phe Gly His Gln Leu Gln Cys Trp
                85                  90                  95

Gln Asp Gly Gly Arg Lys Asn Cys Gly Lys Ser Asp Glu Phe Asn Arg
            100                 105                 110

Met Glu Gly Asp Met His Asn Leu Phe Pro Ala Ile Gly Glu Val Asn
        115                 120                 125

Gly Asp Arg Ala Asn Phe Arg Phe Ser Asp Trp Asn Gly Lys Pro Asn
130                 135                 140

Gln Tyr Gly Lys Cys Gln Met Leu Val Asp Phe Lys Glu Arg Gln Val
145                 150                 155                 160

Gln Pro Pro Lys Gly Pro Val Arg Gly Gln Ile Ala Arg Ala Tyr Leu
                165                 170                 175

Tyr Met Ser Gln Gln Tyr Gly Leu Arg Leu Ala Ala Gln Arg Lys
            180                 185                 190

Leu Tyr Glu Ala Trp Asp Arg Gln Tyr Pro Ala Asp Arg Trp Glu Cys
        195                 200                 205

Glu Arg Asn Arg Arg Ile Gly Lys Leu Gln Gly Asn Thr Asn Pro Phe
210                 215                 220

Ile Glu Lys Gln Cys Gln
225                 230

<210> SEQ ID NO 5
<211> LENGTH: 17
<212> TYPE: DNA
<213> ORGANISM: Artificial
<220> FEATURE:
<223> OTHER INFORMATION: PCR-Primer 341f

<400> SEQUENCE: 5
cctacgggag gcagcag                                                  17

<210> SEQ ID NO 6
<211> LENGTH: 17
<212> TYPE: DNA
<213> ORGANISM: Artificial
<220> FEATURE:
<223> OTHER INFORMATION: PCR-Primer 985r

<400> SEQUENCE: 6
gtaaggttct tcgcgtt                                                  17
```